US005259370A

United States Patent [19]
Howe

[11] Patent Number: 5,259,370

[45] **Date of Patent: * Nov. 9, 1993**

[54] NEBULIZER HEATER

[75] Inventor: Blair E. Howe, Rancho Santa Margarita, Calif.

[73] Assignee: Cimco, Inc., Costa Mesa, Calif.

[ * ] Notice: The portion of the term of this patent subsequent to Nov. 12, 2008 has been disclaimed.

[21] Appl. No.: 774,784

[22] Filed: Oct. 10, 1991

Related U.S. Application Data

[63] Continuation-in-part of Ser. No. 422,310, Oct. 16, 1989, Pat. No. 5,063,921, which is a continuation-in-part of Ser. No. 280,550, Dec. 6, 1988, abandoned, which is a continuation-in-part of Ser. No. 120,080, Nov. 12, 1987, Pat. No. 4,819,625.

[51] Int. Cl.[5] .......... A61M 11/00

[52] U.S. Cl. .......... 128/200.14; 128/203.26

[58] Field of Search .......... 128/200.14, 200.18, 128/200.21, 203.12, 203.25, 203.26, 203.19, 204.13

[56] References Cited

U.S. PATENT DOCUMENTS

| | | | |
|---|---|---|---|
| D. 234,641 | 3/1975 | King et al. | D83/1 N |
| D. 263,337 | 3/1982 | Hart et al. | D24/4 |
| 1,323,181 | 11/1919 | Goodfellow | 128/203.19 |
| 2,882,026 | 4/1959 | Eichelman | 261/2 |
| 3,353,536 | 11/1967 | Bird et al. | 128/194 |
| 3,836,079 | 9/1974 | Huston | 239/74 |
| 4,009,713 | 3/1977 | Simmons et al. | 128/193 |
| 4,674,494 | 6/1987 | Wiencek | 128/204.13 |
| 4,819,625 | 4/1989 | Howe | 128/200.14 |
| 4,951,659 | 8/1990 | Weiler et al. | 128/200.18 |
| 5,063,921 | 11/1991 | Howe | 128/200.14 |

*Primary Examiner*—Edgar S. Burr
*Assistant Examiner*—Aaron J. Lewis
*Attorney, Agent, or Firm*—Poms, Smith, Lande & Rose

[57] ABSTRACT

A nebulizer providing a moistened breathing mixture of aerosol for inhalation therapy is provided with an improved accumulator chamber and heater configured to heat aerosol discharged from the nebulizer so as to most efficiently utilize the heat energy and to most efficiently transfer heat energy from the heater to the aerosol. Passage of the aerosol through and accumulation in a relatively long annular accumulator chamber that adjoins the heater allows introduction of heated water vapor into the aerosol. A central chamber collects precipitated droplets from the mixing chamber, and a wicking disc flows the collected liquid, under pressure or by wicking action, into the accumulator chamber where it is heated and vaporized.

28 Claims, 5 Drawing Sheets

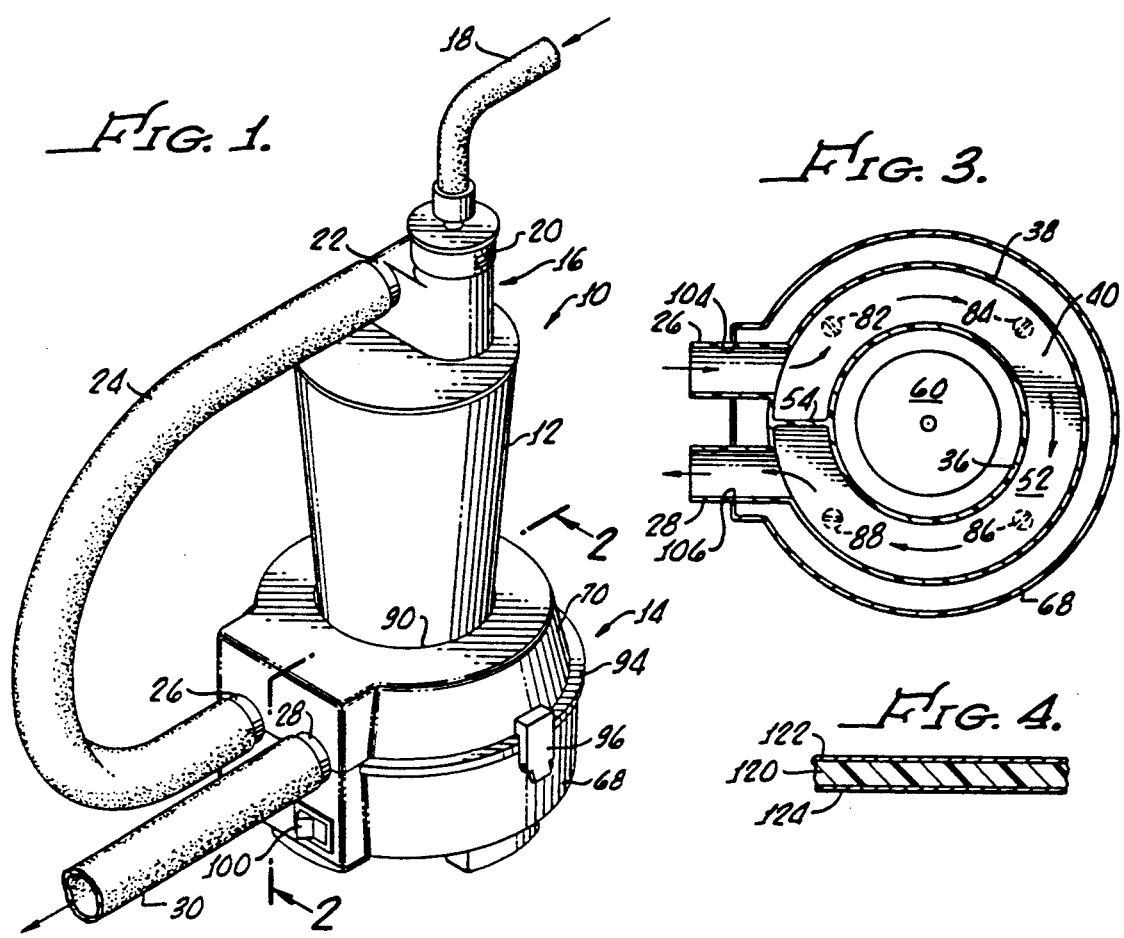
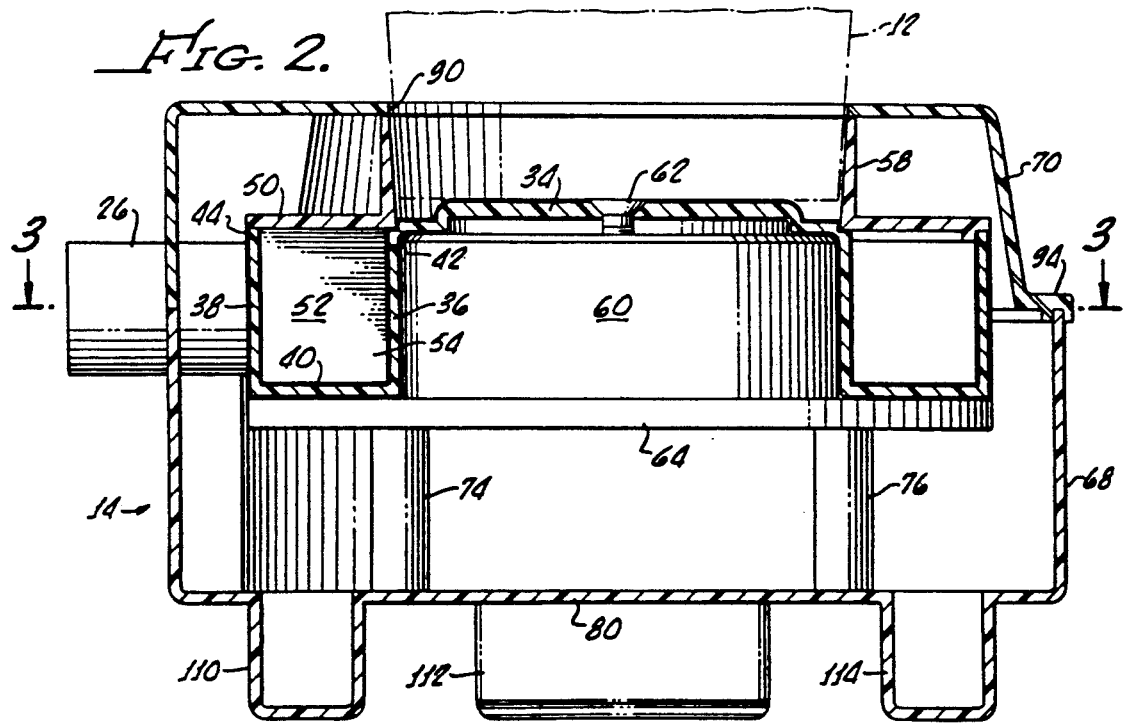

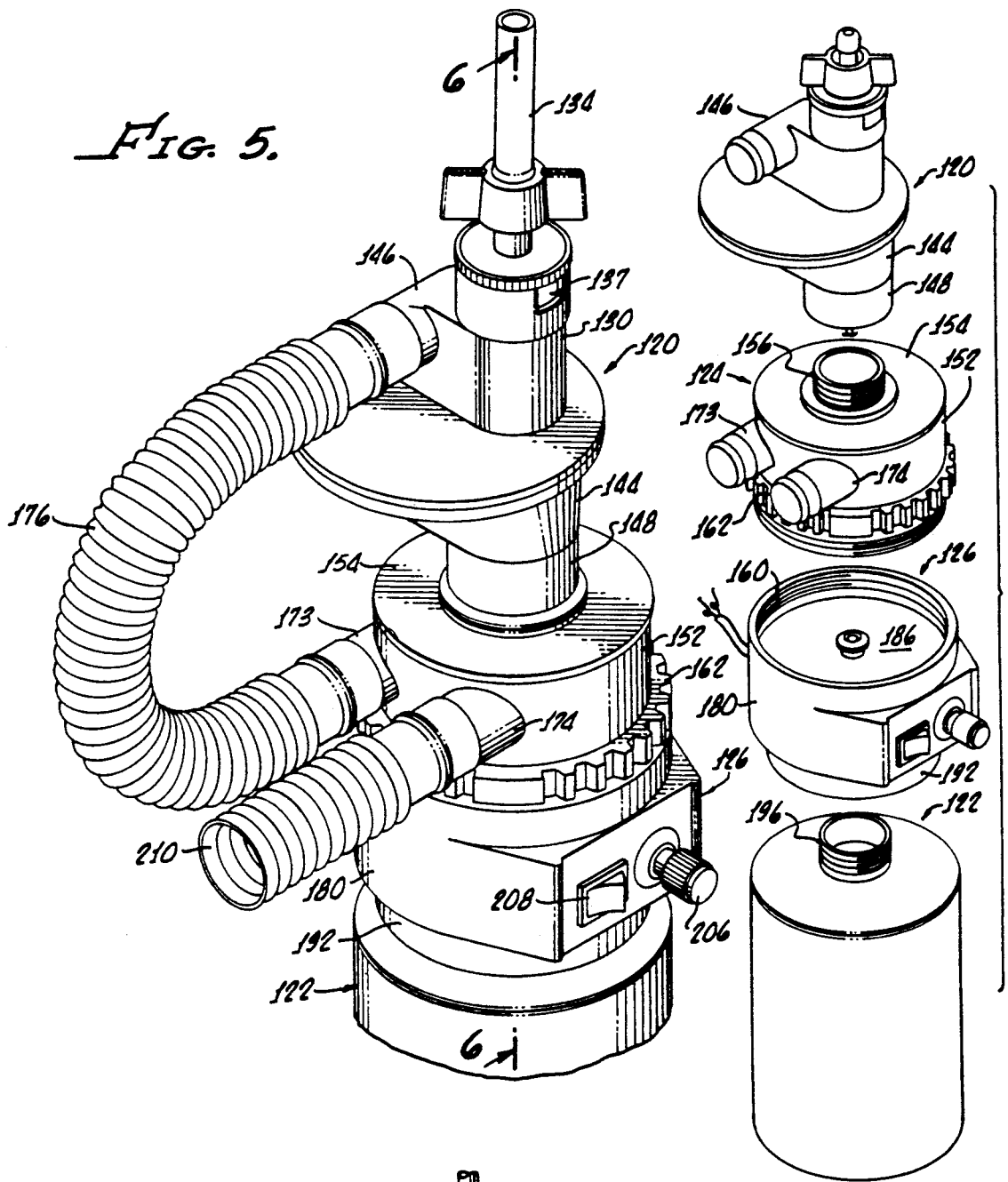
Fig. 5.
Fig. 9.
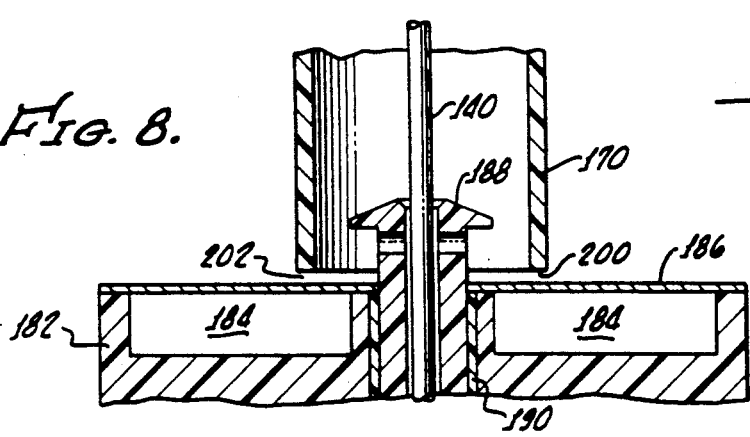
Fig. 8.

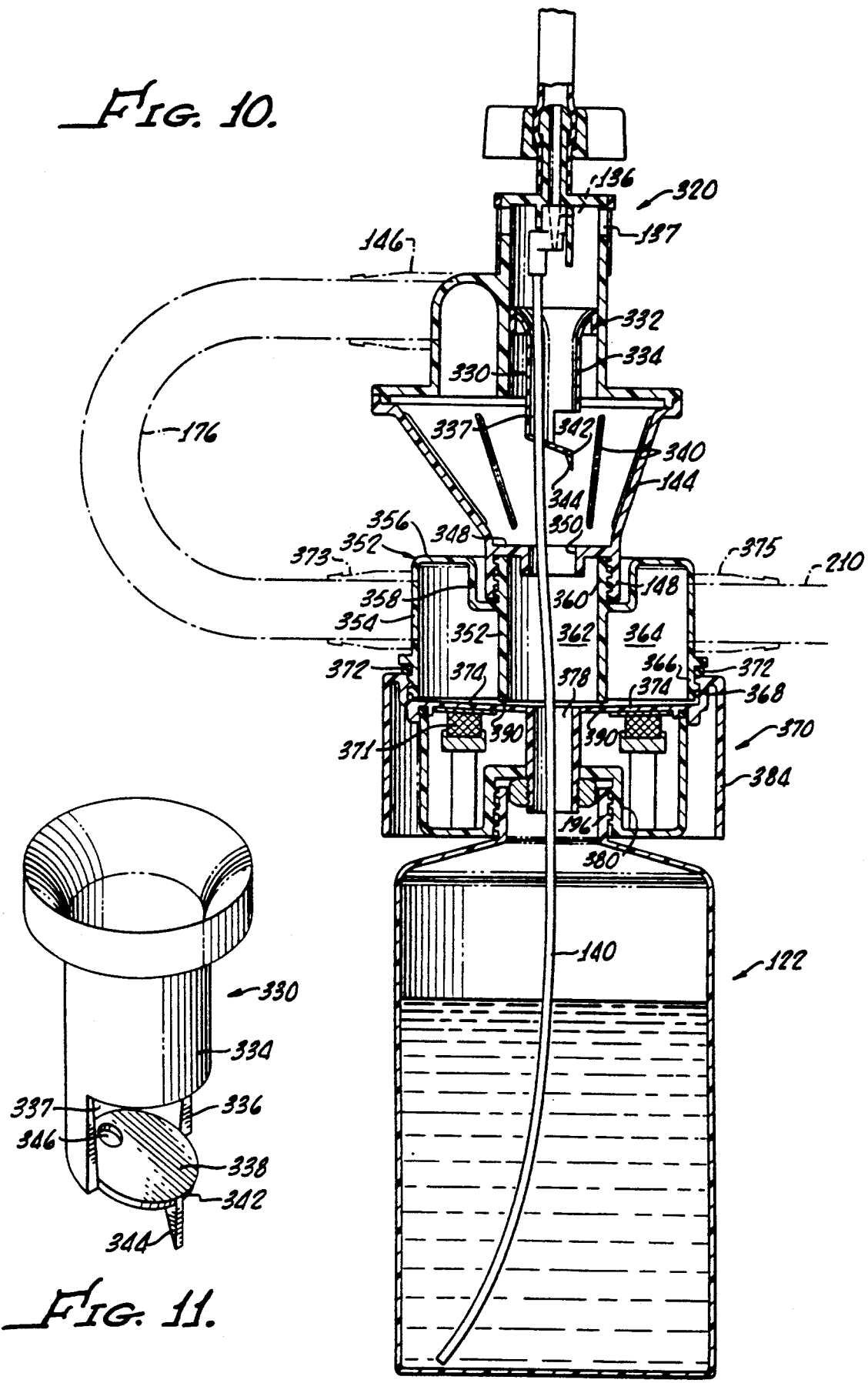

5,259,370

NEBULIZER HEATER

This application is a continuation-in-part application of application Ser. No. 422,310, filed Oct. 16, 1989 for Nebulizer Heater now U.S. Pat. No. , 5,063,921, which in turn is a continuation-in-part of application Ser. No. 280,550, filed Dec. 6, 1988, for Nebulizer Heater (now abandoned), which in turn is a continuation-in-part application of application Ser. No. 120,080, filed Nov. 12, 1987 for Nebulizer Heater, now U.S. Pat. No. 4,819,625.

BACKGROUND OF THE INVENTION

The present invention relates to nebulizers for inhalation therapy, and more particularly concerns a nebulizer having improved arrangements for heating both the container liquid and the aerosol produced by the nebulizer, and for collecting and vaporizing precipitated liquid droplets.

Nebulizers are commonly used for inhalation therapy to provide moist warm oxygen enriched breathing mixture to the patient. In many types of nebulizers a stream of oxygen is passed through a restrictive nozzle to increase its velocity and provide a venturi effect that sucks liquid from a container connected with a mixing chamber. The high speed stream of oxygen is mixed with ambient pressurized air and entrains water that is drawn up from the container by the low pressure of the venturi effect of the oxygen stream of high velocity.

The aerosol breathing mixture reaching the patient must have a temperature not less than ambient room temperature and moreover should have a significant content of water vapor. Various factors tend to lower the aerosol temperature including the relatively long path of aerosol flow through the tubing from the nebulizer to the patient and, in particular, the operation of the air water and oxygen mixing chamber, which often involves a decreased pressure due to at least the venturi action of the high speed jet. In the mixing chamber, expansion of the compressed oxygen will lower its pressure and thus effectively decrease the temperature of the resulting aerosol.

Many attempts have been made to heat either the aerosol or the container liquid but these have not been successful. Nebulizer heaters presently available are considered to be unsatisfactory. It is difficult to heat the aerosol directly, because the mixture. which is basically a gas, has low heat transmissivity, and thus efficiency of prior aerosol heaters has been low. Attempts to heat the aerosol by heating the water in the container before it is mixed with the air oxygen mixture also have been unsatisfactory in that it is difficult to transfer sufficient amounts of heat to the aerosol by means of heating the water. Moreover, having raised the temperature of the resulting aerosol by heating the water, the aerosol becomes more susceptible to "rain out", which means that water vapor in the aerosol tends to condense into larger droplets and to fall from the aerosol into the connecting tubing. The problem of water collecting in the connecting tubing between the nebulizer and the patient is significant, not only because of the fact that the aerosol reaching the patient has less moisture, but because water collecting in the tubing could block the tubing and prevent flow of any inhalation mixture to the patient. No nebulizers are known that increase entrained water content of the aerosol by introducing water vapor produced by a heater.

Accordingly it is an object of the present invention to provide an aerosol heater that avoids or minimizes above mentioned problems.

SUMMARY OF THE INVENTION

In carrying out principles of the present invention in accordance with one embodiment thereof, an accumulator housing connected to a heater housing cooperates with a heated platen to define an aerosol accumulator chamber with a precipitate flow tube extending from the aerosol mixing chamber of the nebulizer mixing body and through the accumulator chamber, to define a peripheral accumulator passage within the accumulator housing, and to define a gap for controlled flow of precipitate from the lower end of the precipitate flow tube to the accumulator passage. Collected precipitate is heated and vaporized in the accumulator passage and returned to the aerosol. The precipitate flow tube is pressurized to aid flow of precipitate to the accumulator passage. One embodiment of the invention maximizes collection of precipitated droplets for flow to the heated accumulator passage instead of return to the liquid container. Aerosol from the aerosol mixing chamber is conducted by a conduit into the peripheral accumulator passage and exits therefrom to provide a heated aerosol stream for inhalation therapy. Introduction into the aerosol of water vapor generated by the heated platen in the bottom of the aerosol chamber enhances both increased moisture content and increased temperature of the aerosol. In one embodiment means are provided to induce controlled flow of collected water to the heater platen.

BRIEF DESCRIPTION OF THE DRAWINGS

FIG. 1 is a pictorial view of a nebulizer and heater embodying principles of the present invention;

FIG. 2 is a section taken on lines 2—2 of FIG. 1;

FIG. 3 is a section taken on lines 3—3 of FIG. 2;

FIG. 4 is a fragmentary sectional view showing details of the coated plastic that forms structural elements of the heater housing;

FIG. 5 is a perspective illustration of a modified form of the nebulizer and modified heater;

FIG. 8 is an enlarged fragmentary view showing the relation between an end of the precipitate flow tube and the heater plate of the embodiment of FIG. 5;

FIG. 9 is an exploded perspective view showing major components of the embodiment illustrated in FIG. 5;

FIG. 10 is a vertical section of another embodiment of nebulizer and heater;

FIG. 11 is a pictorial illustration of a venturi tube and droplet collection plate of the embodiment of FIG. 10;

DETAILED DESCRIPTION

Figure 6:
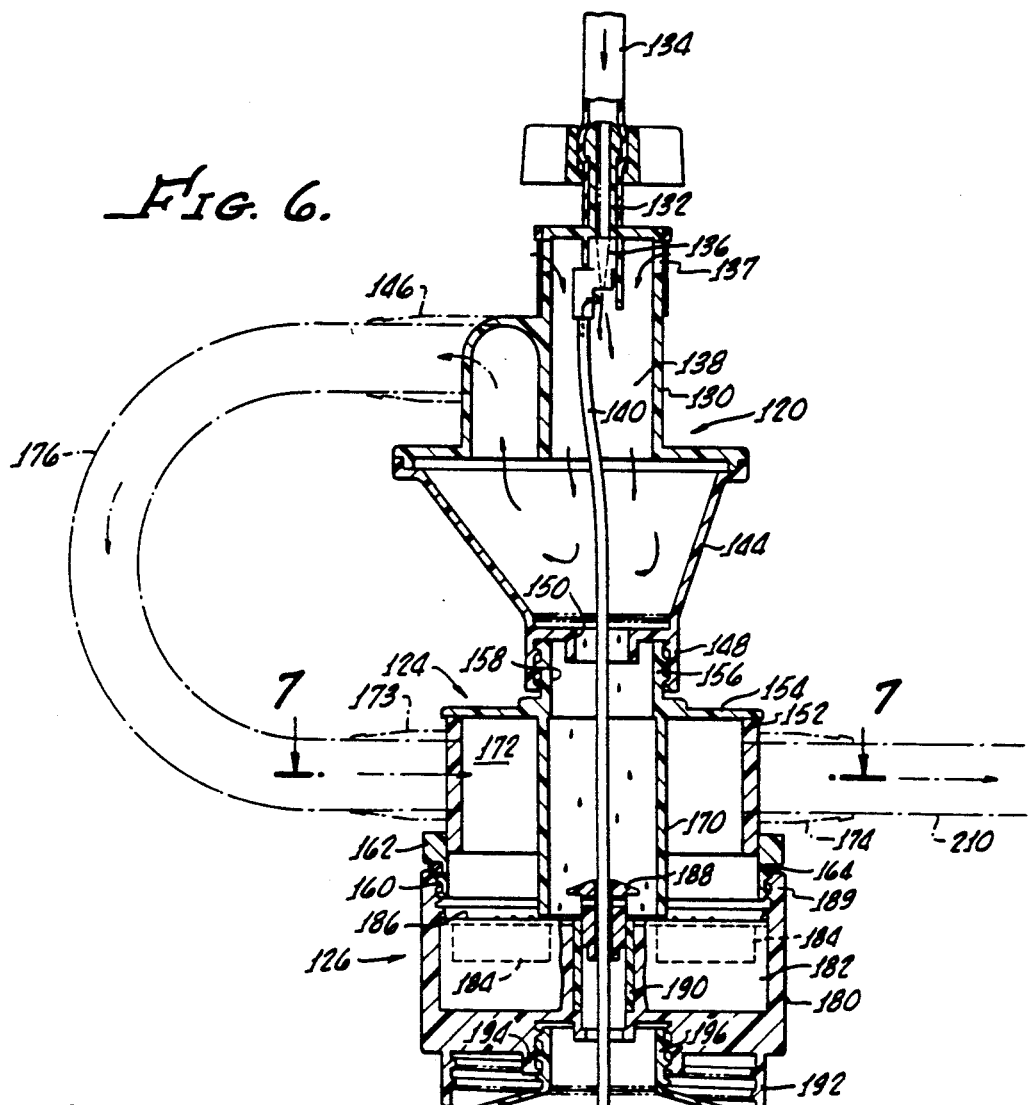
FIG. 6 is a vertical section taken on lines 6—6 of FIG. 5.

As illustrated in FIG. 1 a nebulizer, generally indicated at 10, includes a container 12 having its lower portion resting upon and generally confined in a base type heater, generally indicated at 14. The nebulizer may be of the type shown in U.S. Pat. No. 4,629,590 to Bagwell, which describes a nebulizer sold by CIMCO, assignee of the present application. U.S. Pat. No. 4,629,590 is owned by such assignee. The nebulizer container 12 confines a body of sterile water and includes an upper portion having secured thereto a mixer 16, which receives oxygen under pressure from an oxygen input conduit 18. By means of a mixing jet (not shown in FIG. 1) contained within the mixer 16, liquid is drawn from the bottom of the container 12 for mixing in an aerosol mixing chamber with the pressurized oxygen and with ambient air drawn into the mixing chamber through an aperture 20 in the mixer. Thus, the mixer of the nebulizer provides a output stream, via an output fitting 22, of an aerosol, which is a moisturized mixture of air and oxygen for use in inhalation therapy. Further details of this nebulizer are shown in U.S. Pat. No. 4,629,590. FIGS. 5-9, described below, also show further details of the gas/water mixing jet. The construction details of the gas/water mixing arrangement of the embodiment of FIGS. 5-9 may be used in the embodiment of FIGS. 1-4.

According to the present invention a heater assembly 14 is provided to perform a number of different functions. First, the heater assembly provides a support and a base upon which the nebulizer rests. Second, the heater assembly provides direct heat transfer to the bottom and sides of the bottom of the container 12, to directly heat water within the container. Third, the heater assembly provides an elongated aerosol accumulator of high volume and large cross sectional area for heating the aerosol provided by the nebulizer. This aerosol accumulator receives aerosol produced by the nebulizer via a connecting conduit 24, having one end connected to the nebulizer output fitting 22 and the other end connected to an input fitting 26 on the heater assembly. The aerosol accumulator within the heater assembly terminates in an output fitting 28, to which is connected an output conduit 30 that is connected to a patient breathing apparatus (not shown).

A fourth function of the described heater assembly is its collection of rain out from the aerosol of the nebulizer as it flows through and is temporarily stored in the aerosol passage. The heater assembly heats precipitated water droplets to re-vaporize the water so that it will be again entrained within the nebulizer aerosol.

The heater assembly comprises a heat transfer housing. illustrated in cross section in FIG. 2, having a circular top support plate 34 and a depending continuous peripheral wall 36 fixed to the outer edges of the plate 34. A second continuous peripheral wall 38, spaced from the inner wall 36 and running parallel thereto, completely encircles the inner wall 36 and is fixedly connected to the bottom of the inner wall 36 by a continuous annular bottom wall 40, fixedly secured to the bottoms of both the inner and outer walls 36 and 38. Walls 36, 38 and 40 preferably are integral with top plate 34. Fixedly connected to and extending across upper edges 42, 44 of inner and outer walls 36 and 38 is a continuous annular top wall 50, which cooperates with the sidewalls 36, 38 and bottom wall 40 to provide a sealed completely closed continuous annular aerosol passage and accumulator 52.

As best seen in FIG. 3 tubular input and output fittings 26, 28 are integrally formed with the circular outer wall 38 and a single baffle or partition 54 extends across the aerosol passage, from the inner wall 36 to the outer wall 38, so as to provide a continuous flow aerosol accumulator passage and temporary storage chamber. Aerosol will flow in through fitting 26, thence in a clockwise direction, as indicated by the arrows, around the aerosol accumulator passage 52, and thence outwardly through output fitting 28. Aerosol remains in the accumulator 52 because of its relatively large volume and because its cross sectional area is made larger than that of the input and output ports and conduits.

A relatively short rigid upstanding container support wall 5 is fixed to the outer edge of top plate 34 and to the upper edge of inner wall 36 and extends continuously around the bottom of container 12 to confine the bottom of the container within a heater recess formed by support wall 58 and top plate 34. Top plate 34 and inner wall 36 cooperatively define a downwardly facing heater mounting chamber of generally circular cylindrical form which snugly mounts a circular cylindrical and heat conductive heater housing 60 containing suitable heater elements (not shown). Heater housing 60 may be secured within the heater chamber and to the top plate 34 by means of fastener means such as for example a screw 62. Heater housing 60 includes a heater housing bottom plate 64 of circular configuration and extending along and in heat conductive contact with the full extent of bottom wall 40, to provide maximum heat flow from the heater to the bottom plate.

The heat transfer housing and the heater housing 60 are mounted in a heater assembly housing formed of an inter-fitting base 68 and a heater assembly housing top 70. Housing base 68, formed of a suitable rigid plastic, is of a circular configuration, having four mutually spaced and fixed internal supporting posts 74, 76, and others (not shown) projecting upwardly from a bottom 80 of the base 68. Each post has a vertically extending threaded aperture for receiving respective ones of a plurality of screws 82, 84, 86 and 88, (FIG. 3) which extend through the heater housing bottom plate 64 into the apertures in supporting posts 74, 76 etc. The assembly housing top part 70 has a central aperture 90, through which the bottom of the container 1 extends for support by the heater top support plate 34. Inner edges of the apertured top of assembly housing top 70 rest on upper edges of container support wall 58. A peripheral flange 94, outwardly extending from the assembly housing top, cooperates with a pair of oppositely positioned pivoted latches 96 (only one of which is shown) mounted on the assembly housing base 68 to detachably secure the two parts of the assembly housing to one another. A manually operable switch 100, (FIG. 1) mounted on the assembly housing base 68 is provided to control the heater elements which are connected to a suitable source of electrical power by means of an electrical lead and temperature regulating circuitry or the like (not shown), that may be mounted within assembly housing base 68 below the heater housing bottom plate 64. The top and bottom parts of the assembly housing are provided with mating semicircular recesses to form circular apertures (FIG. 3) 104, 106 through which the fittings 26 and 28 extend.

The entire heater assembly is supported on four legs, of which three, indicated at 110, 112, and 114 are shown, which are formed integrally with and depend from the bottom 80 of the bottom part of the heater assembly base 68.

Heater housing 60 and its bottom plate 64 are made of a suitable metal having high heat conductivity such as for example aluminum, whereas the heat transfer housing is made of a light weight plastic having improved heat transfer and cleaning characteristics provided by a heavy metal coating. Thus, as illustrated in FIG. 4, the heat transfer housing including top support plate 34, walls 36, 38, and 40, (but not walls 50 and 58) are formed of a plastic material 120 coated on both sides with heavy, thick coatings 122, 124 of suitable metal. Presently preferred for such coatings are combinations of electroless copper, electroless nickel and chromium, formed in layers, one upon the other and deposited upon both sides of the interposed plastic 120. By this means the plastic is provided with good heat transfer characteristics and a smooth easily cleaned surface, and the parts are still readily manufactured of inexpensive and readily formed plastic. The entire heat transfer housing is readily removable for sterilization. Walls 50, 58 are made of the same plastic as the other walls, but need not be coated with metal.

In operation of the device, oxygen under pressure is fed to the mixer 16 via oxygen input conduit 18 and mixed with fine water droplets or vapor derived from water contained in the container 12 to provide an aerosol discharge via fitting 22 and connecting the conduit 24. The aerosol flows from the conduit 24 through heater assembly input fitting 26 and thence in a substantially 360 degree path through the aerosol accumulator and passage 52 which closely encircles the heater chamber that contains the heater housing 60. Aerosol remains in the accumulator for a relatively increased time. Aerosol then flows through the output port 28 to connecting tubing 30. The container 12, which is resting upon heat transfer housing plate 34 and confined within the circular container support wall 58, has its contents heated by transfer of heat from the heater through the plate 34. Temperature of the aerosol is raised by using water heated in the container by the heater and also by temporarily retaining the aerosol in the accumulator adjacent the very same heater that heats the container. Flow of aerosol through the passage or accumulator 52 is of long duration. Thus, time of storage in accumulator 52 is sufficient to heat the aerosol. Moreover, liquid collecting in the bottom of the passage, due to rain out from the aerosol, is heated, vaporized and recombined with the flowing aerosol. Thus the described heater is effective not only to heat the aerosol provided from the apparatus but also significantly improves its moisture content.

The entire apparatus is readily disassembled for cleaning and sterilization. To disassemble the apparatus, latches 96 are disengaged and the hoses are disconnected. Container 12 is removed from the heater assembly and the assembly housing top 70 is removed from the base 68. The heat transfer housing, comprising the walls 36, 38, top support plate 34, bottom plate 40, and walls 50 and 58 are readily removed as an integral unit from the heater housing 60 which remains fixably secured to the assembly housing base 68 by means of the screws 82 through 88. The heat transfer housing may then be readily cleaned and sterilized. The chromium plated surfaces of the aerosol passage and of the heat transfer housing top plate 34 are smooth and readily cleaned and sterilized.

The described heater assembly is easily adapted for use with nebulizers of different types and different configurations. It is only necessary to change the configuration of the container receiving recess defined by the top support plate 34 and support wall 58, and also the size of opening 90, to enable the heater to receive, support and operate upon a nebulizer having a container of different size, shape or configuration.

The assembly housing provides protection for the heating unit and the heat transfer housing. It prevents heat loss and also protects the controls and electric elements from accidental spillage of water. The housing serves as an insulator and also prevents accidental contact with electrical elements within the assembly housing base.

As mentioned above, a significant aspect of the described construction and configuration of the heater is the fact that the aerosol accumulator or passage not only has a relatively large volume but also has a large cross sectional area. In a presently preferred embodiment the cross sectional area of the annular aerosol passage 52 is approximately twice the cross sectional area of either of the conduits 24 or 30, which are of a size normally employed in devices of this kind. The increased volume and area of the aerosol passage provides a number of advantages. The large volume causes the annular passage to act as an accumulator or reservoir so that aerosol produced by and discharged from the mixer 16 is effectively stored in the passage 52 for a period of time before it is discharged through the relatively small cross sectional area output port 28. Thus, because the formed aerosol is stored for a short period of time within the accumulator or chamber 52, there is more time for large water droplets to be precipitated from the aerosol and, importantly, there is more time for the accumulated water already precipitated in the accumulator chamber to be vaporized and re-introduced into the aerosol within the accumulator chamber. Another advantage of the relatively large cross sectional area of the accumulator 52 is the fact that it has a larger surface area to provide a much greater area of contact between its heated wall and the aerosol that is temporarily stored therein.

In the embodiment illustrated in FIGS. 1 through 4, the nebulizer and container are made and sold as an integral sealed unit complete with a container carrying its body of sterile water. Some nebulizers are made with the mixing head separate from the container and are arranged to be connected at the time of use to a separately manufactured, handled and stored sterile water container. In such an arrangement the nebulizer mixing head is generally provided with a lower portion having a female thread that is adapted to mate with a male thread on the top of a separate container of sterile water, with the nebulizer suction tube withdrawing water from the container into the mixing chamber under the nebulizer venturi action, the suction tube being extended from the nebulizer head down into the container when assembled.

Principles of the present invention may be arranged for use with such a combined assembly of separate nebulizer mixing head and separate sterile water container in a manner illustrated in FIGS. 5 through 9. As shown in FIG. 5, a separate nebulizer head and mixing means is identified generally by numeral 120 and is combined with a separate and independent sterile water container, indicated by reference numeral 122 (only the upper portion of which is shown in FIG. 5). These major components are illustrated in the exploded (disconnected) view of FIG. 9. Commonly, nebulizer head 120 is connected directly to the container 122. However, according to principles of the present invention, as incorporated in the embodiment of FIGS. 5 through 9, an aerosol accumulator housing 124 and a heater assembly 126 are interposed between the mixing head 120 and container 122 with all four units threadedly interconnected to one another in an end to end relation, as can be seen in FIGS. 5 and 6. The nebulizer mixer head comprises a mixer body or housing 130 (FIG. 6), having an input fitting 132 to which may be connected a hose 134 which itself is connected to a source of oxygen under pressure (not shown). Mixer body 130 includes a nozzle fitting 136, having a high velocity jet orifice for introducing pressurized oxygen from tube 134 to the interior 138 of the mixer body. A suction tube 140 is connected to nozzle fitting 136 and has an outlet orifice adjacent the jet orifice. Suction tube 140 extends downwardly through all of the components and has a lower suction end thereof submerged in a body of liquid (generally sterile water) 142 confined in container 122. One or more ports 137 are formed in mixer body 130 for introducing ambient air to the interior of the mixer body to be mixed with the oxygen and water.

Mixer body 130 includes a downwardly tapered aerosol mixing chamber housing section 144, in communication with the interior 138 of the body 130, and an output fitting 146 for discharging mixed aerosol from the aerosol mixing chamber 144. The lower end of chamber 144 is formed with an internally threaded connecting nipple 148, and at its lower end has a relatively large diameter passage 150 for allowing water droplets precipitated from aerosol within the mixing chamber 144 to flow or fall downwardly from the chamber.

An accumulator 124 includes a housing 152 of generally right circular cylindrical configuration, having a fixed top plate 154 formed with an upwardly extending externally threaded connecting fitting 156, having a bore 158, and adapted to threadedly engage the lower threaded fitting 148 of the aerosol mixing chamber.

Accumulator housing 152 has an open bottom end formed with external threads 160 and includes an external circumferential serrated ring 162 just above its threaded end to facilitate turning of the accumulator housing. A sealing o-ring 164 extends around the connecting fitting of the accumulator housing at the upper end of threads 160.

Figure 7:
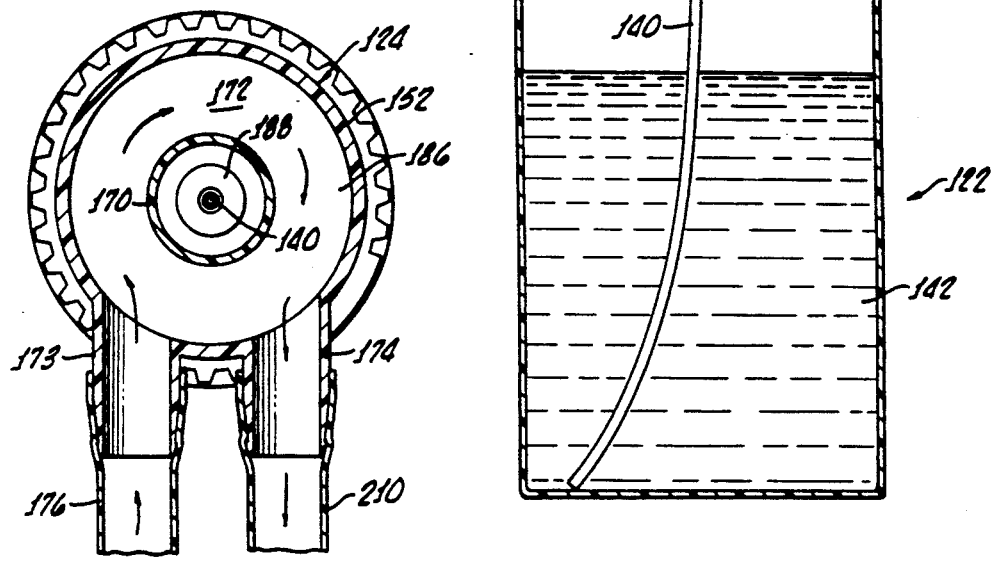
FIG. 7 is a horizontal section taken on lines 7—7 of FIG. 6.

Fixed to the top plate 154 of the accumulator housing, in substantial alignment and coextensive with the interior bore 158 of connecting fitting 156, is a precipitate flow tube 170, of circular cross section, extending downwardly for substantially the full height of the accumulator housing. The precipitate flow tube 170 cooperates with the exterior wall of the accumulator housing to effectively define an annular aerosol accumulator passage 172 within the interior of the accumulator housing and surrounding the tube 170. Input and output fittings 173 and 174, respectively, are connected to input and output ports formed in the accumulator housing and positioned as best shown in FIGS. 5 and 7. Input and output fittings 173 and 174 are illustrated in dotted lines in FIG. 6 as being on opposite sides of the accumulator housing but are shown in such positions solely for clarity of illustration and to enable the showing of both such fittings in the vertical section of FIG. 6. The correct position of fittings 173,174 is as shown in FIGS. 5 and 7. A connecting conduit 176 (FIG. 5) interconnects output fitting 146 of the nebulizer head with the input fitting 173 of the accumulator housing. The actual position of this connecting conduit is outside of the nebulizer head 120 and outside of accumulator housing 124, as shown in FIGS. 5 and 7, but the conduit is shown in dotted lines in FIG. 6 to provide a full, but somewhat schematic, showing in this figure of the interconnection of the accumulator and mixer head.

Heater 126 is formed with a substantially right circular cylindrical housing 180, defining a heater chamber 182 in which is mounted an annular shaped heater 184 (FIG. 8). Heater 184 is in contact with a heater platen 186 (see FIGS. 6 and 8) which extends across and seals the upper end of the heater chamber 182. The heater plate is a thin metallic plate, sealing the heater chamber but having a central opening in which is seated an apertured grommet or sealing plug 188. Suction tube 140 extends from the fitting 136 downwardly through the aerosol mixing chamber 138, through the precipitate flow tube 170, completely through the aperture of the sealing plug 188, through the center of the heater chamber 182, and into the liquid 142 contained in container 122. The plug 188 collects and sheds water droplets that collect on the suction tube and prevents such water from flowing back into the container. The plug sheds such collected water to the heater platen to flow beneath the lower end of tube 170 into the accumulator chamber.

Heater housing 180 has an upper end portion 189 internally threaded to receive the external threads 160 of the lower connecting end of the accumulator housing, so that when the accumulator housing and heater housing are connected as shown in FIG. 6, sealing o-ring 164 is compressed between the upper end of the heater housing and the serrated ring 162, to seal the two together. A centrally located cylindrical member 190 extends vertically through the heater housing, receiving the lower end of sealing plug 188 and providing a central guideway for the suction tube 140.

The lower end of heater housing 180 is formed with a threaded connecting fitting, having two concentric internal connecting threads of mutually different diameters. Thus, a large diameter connecting thread 192 is provided for threaded connection with a container (not shown), having a relatively large diameter male connector at its upper end. The lower end of the heater housing also has a smaller diameter internally threaded connector 194 that threadedly connects to the externally threaded neck 196 of container 122. Although the assembly is shown as composed of four basic units, mixer head 120, accumulator chamber 124, heater 126, and container 122, all threadedly interconnected to one another in end to end relation, it will be readily appreciated that any two or more of the four components parts may be made with fixed interconnection between them. For example, the mixer head, accumulator housing and heater all may be fixedly and permanently connected to one another. In such an arrangement this assembly of the three upper components is capable of being detachably and threadedly connected to an independent, separate sealed sterile container, such as container 122. Alternatively, the accumulator housing and heater may be permanently connected to one another, and appropriate threaded fittings provided on the upper end of the accumulator housing and the lower end of the heater for connection to different types of aerosol mixing heads and sterile containers.

An important feature of the present invention is the position and relative location of the lower end of precipitate flow tube 170. This is best shown in FIGS. 6 and 8. The lower end 200 of tube 170 is positioned closely adjacent to but spaced from the heater platen 186 to provide a flow gap 202 that is approximately 0.03 inch in height. Water droplets, liquid precipitate, falling from the aerosol in aerosol mixing chamber 138, 144, drop through the bore 158 of the lower end fitting 148 of the aerosol mixing chamber, and then through the precipitate flow tube 170 to fall upon the upper surface of heater platen 186, which is heated directly by the heater element 184. Droplets also collect on the interior of chamber walls 144 and upon the exterior of the suction tube 140 (in the mixing chamber) and flow downwardly along the surfaces to be collected at the lower end of tube 170. The heater is such as to provide a temperature of the platen of as high as 130° C. Temperature of the heater platen is adjustable by means of a temperature control knob 206, FIG. 5, and power to the heater is controlled by on/off switch 208. With heater platen temperatures at or near boiling, water droplets falling through the flow tube 170 to the heater platen are quickly heated and are drawn from or caused to flow outwardly from the area of the heater platen directly underneath the flow tube 170 radially outwardly into the peripheral aerosol accumulator chamber 172. These water droplets are caused to flow radially outwardly through a capillary passage formed by the gap 202 by a combination of forces, including a capillary action that results from the very small size of the gap 202 and the increased pressure in the interior of mixing chamber 144. This increased pressure is caused in part by the pressurized oxygen input from oxygen input tube 134. The accumulator chamber is connected via its output port 174, and therefore is at substantially ambient pressure, to provide a differential pressure between mixing chamber 144 and the accumulator chamber that helps drive water through the gap. The very small gap ensures that precipitated water droplets not only contact the heater platen 186, but are caused to flow along its surface, and thus remain in contact with the heater platen for an increased period of time, thereby increasing the efficiency of the water vaporization that is accomplished by the heater plate. The heater platen vaporizes water droplets precipitated from the aerosol mixture in the mixing chamber 144 and also those droplets precipitated from the aerosol flowing through the accumulator passage 172. Heated water vapor is thus generated by the heated platen at the bottom of the accumulator passage 172 and is mixed with aerosol in the passage. This accomplishes two desired results. The heated vapor efficiently increases aerosol temperature and efficiently increases moisture content of the aerosol.

In operation of the nebulizer and heater of FIGS. 5-9, oxygen flowing under pressure from input tube 134 is projected at high velocity from the orifice of jet nozzle fitting 136, providing a slightly lower pressure that accompanies the high speed oxygen stream adjacent the upper end of the suction tube 140. Enough suction is created by the high velocity stream to draw liquid from the container 122, through the suction tube into the mixing chamber 138. Ambient air is also drawn in through ports 137 to provide an aerosol mixture of water, oxygen and air that flows downwardly into the aerosol mixing chamber 144. The aerosol swirls about and is mixed in this chamber, then flows through the discharge port 146, through connecting conduit 176, and into the aerosol accumulator passage via input fitting 173. The aerosol flows around the passage 172, in the directions indicted by the arrows in FIG. 7, and after one or more revolutions will flow outwardly through output fitting 174, where it is fed via an output tube 210 to a patient's breathing apparatus. The aerosol dwells for a relatively long time in the long peripheral passage 172 of the accumulator, and thus is effectively heated by the platen 186.

During passage of the aerosol through the accumulator chamber, water droplets that have fallen through or flowed along walls of precipitate flow tube 170 and have flowed along the outside of the suction tube collect at the bottom of the precipitate flow tube. The collected droplets are driven through narrow gap 202 to be vaporized by the heater platen 186 and are reintroduced as heated vapor into the aerosol for flow to the patient. Precipitate from the aerosol mixing chamber 144 is initially collected on an area of the heater platen within the flow tube and, under the differential pressure across the gap, flows into the accumulator passage along the heater plate, providing longer and closer contact between the precipitate and the heater platen and, thereby, a more efficient heat transfer. Larger water droplets in the aerosol that flows around the aerosol accumulator passage may be precipitated from the aerosol while the latter is in the accumulator passage. These are also accumulated within the passage 172, to be collected on the heater platen 186 which forms the bottom of the passage. This water is also re-vaporized by the heater platen for re-entrainment in the aerosol produced by the system.

It is found that the described heating arrangement is exceedingly efficient and provides surprising and greatly unexpected temperature increase for a given amount of heater power. In an arrangement of the mixer body 120, heater 126 and container 122, connected without the accumulator chamber 124 (the latter may be omitted from the assembly by providing an adapter plate having a fitting at its upper end that mates with the mixing chamber fitting and having its lower end mating with the heater housing threads), the heater was set to a temperature sufficient to provide a temperature of output aerosol in output tube 210 of between 92° and 94° F., and required heater power was measured. The accumulator unit 124 then was interposed between the mixer body and heater, as described herein. Use of the accumulator provided the same output temperature of between 92° and 94° F. with only twenty percent of heater power required to obtain such temperature without the accumulator 124.

Illustrated in FIGS. 10 and 11 is a modified version of the heated nebulizer of FIGS. 6 through 9 which has changes made primarily to improve collection and vaporization of precipitated water droplets and to provide a wider range of adjustment of vapor content and temperature of the aerosol fed to the patient. The embodiment of FIGS. 10 and 11 is identical to that of FIGS. 6 through 9 except for addition of a venturi tube and modifications in heater and accumulator configuration. Identical parts in the two embodiments are designated by like reference numbers.

The nebulizer head 320 of FIG. 10 is identical to the head 120 of FIG. 5, except for the addition of a venturi tube 330. Tube 330 both increases flow velocity of aerosol into the mixing chamber 144, and, importantly, provides improved precipitated droplet collection. Venturi tube 330 is fixedly positioned within the neck 332 of the mixer body below the nozzle fitting 136 and has a lowermost portion of its shank 334 cut away to form a large opening, as at 336. One side 337 of the shank extends downwardly to the end of the venturi tube 330 and has fixed thereto a downwardly inclined bottom plate 338. The bottom plate inclines downwardly toward the wall 340 of the mixing chamber that is closer to the axis of the mixing head and venturi tube, in this asymmetrical arrangement of the mixing head that is shown in the drawings. The lowermost free edge 342 of plate 338, which is offset laterally from the axis of the mixing head and the axis of the venturi tube, has a downwardly projecting wedge shaped and pointed drip member 344 fixed thereto. The plate also has an aperture 346 that snugly receives suction tube 140.

Venturi tube 330 acts to increase the velocity of the gas jet projected from nozzle fitting 136 and also, by means of its bottom plate 338, collects water droplets. These collected droplets flow to the free edge of the plate and then along the drip wedge 344 to drop from the point at its lower end. The pointed end of drip wedge 344 is positioned above the inwardly projecting floor 348 of the mixing chamber, and thus droplets from the wedge 344 and also droplets flowing downwardly along the interior walls of the mixing chamber tend to collect on the bottom wall 348 of the mixing chamber to flow downwardly through the aperture 350 thereof.

Droplets in the aerosol tend to collect on various surfaces, including the suction tube above the bottom plate 338. The snug fit of the bottom plate hole 346 around the exterior of suction tube 140 blocks the flow of collected droplets on the exterior of the suction tube and diverts these droplets along the bottom plate to the drip wedge and then into the accumulator passage, as will be described below.

Accumulator housing 351 includes a circular outer wall 354 and a circular inner wall 352 concentric therewith and integrally connected with the outer wall by an upper wall 356. The latter has an inner stepped vertical portion 358 that is spaced radially outwardly of an upper end portion 360 of the tubular inner wall 352. Tubular wall 352,360 defines an inner or precipitate chamber 362 and cooperates with outer wall 354 to define the outer annular accumulator flow passage 364. The upper portion 360 of the tubular wall of the precipitate flow chamber 362 is radially spaced inwardly from the accumulator passage wall 358 and is externally threaded to receive the internally threaded connecting nipple 148 of the mixing chamber 144. The accumulator chamber housing has a lower end portion 366 that is externally threaded to receive internal threads on an upper portion 368 of heater housing 370. An o-ring 372 has a relatively large diameter and is sufficiently resilient and deformable to enable adjustment of temperature and moisture content, as will be described below.

Heater housing 370 includes a heater chamber in which is mounted an annular heating element 371 positioned below a heated platen 374 that forms the top of the heater housing and, concomitantly, the bottom of the accumulator chamber 364 and the bottom of precipitate or droplet flow chamber 362. The heater element extends only under the annular accumulator chamber and not under the precipitate flow chamber 364. A tubular drain opening 378 extends through the heater housing and has an upper end substantially flush with the upper side of platen 374. Opening 378, extending vertically through the heater and its platen 374, has a relatively large unrestricted diameter for free reception of the suction tube 140. Accordingly, it is relatively easy, when assembling the mixer to the accumulator and heater units, to insert the free end of the long, slender and flexible suction tube 140 (having its upper end already attached to the nozzle fitting 136) through the accumulator and heater units without any hands touching the suction tube. The large size of these openings, in both accumulator housing and heater, allows the operator to hold only the mixer body and manipulate the free end of the long, flexible suction tube through the openings of the heater and accumulator units with little difficulty.

The lower end of the heater housing includes an internally threaded fitting 380 for threaded engagement with the externally threaded neck 196 of a liquid container, and, if desired, may also have a larger threaded opening (not shown), just as is illustrated with the heater assembly of FIG. 6, for reception of a container having a larger diameter threaded neck.

Integrally formed with the heater housing is a peripheral skirt 384 that is radially outwardly spaced from the walls of housing 370 to act as a heat shield so that the heater assembly provides a relatively lower temperature exterior surface.

Heated platen 374 is slightly dish-shaped, that is, concave upwardly, having a slope in the order of 2° to 3° from its outer peripheral edge downwardly toward the center of the plate at the upper end of tubular opening 378. Just as in the embodiment of FIG. 6, a flexible connecting tube 176 is connected at one end to the mixing head discharge port 146 and at the other to the input port 373 of the accumulator housing, which also has an output port 375 adapted to be connected via a conduit 210 to a patient.

An important feature of the described arrangement is adjustability of the water flow gap between the bottom end 390 of tube 352 and the heated platen 374. As previously mentioned, the o-ring 372 is relatively large, resilient and deformable. Further, the threads on parts 366,368, which interconnect the accumulator housing and heater housing, have a steep pitch. Accordingly, a small degree of rotation of the accumulator housing relative to the heater housing will axially shift the accumulator relative to the heater but will still maintain sufficient compression of the o-ring 372 so that the two are still sealed together. This small amount of axial relative shifting will change the size of the gap at the bottom end 390 of the precipitate flow chamber, and thus will adjust the amount of water that flows from the precipitate flow chamber 362 to the accumulator chamber 364. By adjusting the gap between the precipitate flow chamber and the accumulator chamber one can adjust the amount of heated water vapor that is added to the aerosol in the accumulator chamber. Thus temperature and moisture content of the aerosol discharged to the patent are both adjusted, merely by relative rotation of the accumulator housing and heater housing.

If desired, the adjustment is arranged so that the gap can be adjusted down to a very small size, such that effectively no water will flow from the precipitate flow chamber 362 into the accumulator chamber. Preferably, a rotation stop (not shown) is provided such that there is a limit on the minimum size of the gap which, therefore, is never completely closed and will always allow some water to pass. Normally, however, the gap is adjusted to about 0.030 inches so that there will be an adequate flow of water for vaporization and combining with the aerosol in the accumulator chamber. For adjustment of the gap, it may be desirable to provide indicia on the accumulator housing and heater housing to indicate a desired amount of relative rotation, and, therefore, the gap size.

The heated nebulizer of FIGS. 10 and 11 operates substantially in the same way as the heater nebulizer of FIGS. 6 through 9. Pressurized oxygen is introduced through the nozzle fitting to the interior of the mixer body to suck water from the liquid container 122 via suction tube 140. The suction tube extends from the container through the heater, through the droplet flow passage 362, which is circumscribed by the accumulator flow passage 364, and through the aerosol mixing chamber. Ambient air is also pulled into the mixing head through the ports 137 so that the aerosol stream is projected downwardly through and axially along the center of venturi tube 330. The stream impinges upon the bottom plate 338 and is directed radially outwardly toward the walls of the mixing chamber 144, which may be provided with shallow ribs 340 extending substantially vertically along the walls from top to bottom and spaced circumferentially about the mixing chamber. As the aerosol is directed somewhat radially outwardly from the bottom plate 338, it tends to travel in a circular path about the aerosol mixing chamber, impinging upon the ribs 340, which thus aid in precipitation of large droplets of aerosol. These droplets are collected along the walls of the aerosol mixing chamber and flow down through opening 350 to accumulate at the lower end of precipitate flow chamber 362.

It is important to note that the lower end 390 of the tubular wall 352, which defines the precipitate flow chamber 362, is spaced slightly above the upper surface of the dish-shaped heated platen 374 to provide a liquid flow gap for flowing liquid from the bottom of the flow chamber 362 into the accumulator chamber 364 along the platen 374. This flow is assisted by the pressurization of the interior of chamber 362, caused in part by the pressurized oxygen coming into the mixing head. Pressure within chamber 362 is of course communicated to the interior of the closed and sealed liquid container 122, but the accumulator chamber 364 has its output port effectively connected to the patient, and therefore to ambient pressure, which is lower than the pressure within the precipitate flow chamber 362. Accordingly, the pressure difference across the gap at the bottom 390 of the precipitate flow chamber ensures flow of the collected liquid into the accumulator chamber. Droplets are also collected by the venturi tube bottom plate 338, which blocks flow of liquid that adheres and to and tends to flow downwardly along the exterior surface of the suction tube 140. Plate 338 and its drip wedge 344 tend to direct such collected droplets to the bottom 348 of the aerosol mixing chamber, from whence it flows downwardly through the precipitate tube 352, to be collected at the bottom of chamber 362. The drip wedge 344 helps to prevent water running downwardly along the upper surface of the plate 338 over the lower edge and then back up along the bottom side of the bottom plate toward the pickup tube 140. As the liquid flows through gap 390 along the heated platen to the bottom of the accumulator flow chamber 364 it is heated and at least some is vaporized by the high temperature of this outer annular section of the heated platen. Thus heated water vapor is generated to mix with the aerosol within the chamber 364, thus increasing both its water content and temperature. By adding heated water vapor, temperature of the aerosol mixture is most efficiently increased.

The described arrangement of FIGS. 10 and 11 includes a safety feature that prevents significant overheating, such as may cause danger to the operator and deformation or destruction of the mixer head. If the oxygen supply is turned off without turning the heater off, water contained in the bottom of the accumulator chamber 364 will flow radially inwardly along the tapered platen to the drain tube 37 and drain back into the container itself. If provision were not made for draining of water from the accumulator chamber upon shut off of the oxygen, water contained within the accumulator chamber 364 would start to boil upon shut off of the oxygen, since there would be no longer any flow through the accumulator passage. Steam then would tend to fill the accumulator passage and flow back up through the connecting tube 176 into the mixer head itself. The latter is made of a plastic that may tend to deform at temperatures in the order of 100° C. or less, and thus can be seriously damaged by being filled with steam. Moreover, the heater and other parts of the instrument may become excessively hot to the touch if steam continues to be generated after oxygen is turned off. However, this is not possible with the described arrangement, because the water will drain back to the container and will not be boiled or turned into steam. Moreover, the heat shield 384 helps to maintain a lowered external temperature of portions of the instrument adjacent the heater.

An advantage of the recessing of threaded portion 360 of the accumulator housing within the accumulator housing itself is the fact that this decreases the overall height of the instrument, and, in particular, decreases the distance between the liquid container 122 and the mixing head. The nebulizer nozzle fitting pulls liquid from the container by means of suction produced by the high velocity jet, and is able to suck liquid over only a limited vertical distance. The less the length (vertical extent) of the accumulator and heater units, which are interposed between the mixing head and the container, the less the distance through which the liquid need be drawn up from the container.

The described apparatus is considerably quieter than prior nebulizers, providing less jet venturi noise from the mixing head and considerably less noise in the tube that connects the accumulator output to the patient. The decrease in noise in due in part to the multiple chambers and the flow paths for the aerosol.

Prior nebulizers are limited in the amount of flow rate available, because if flow rate is increased, the temperature of the generated aerosol is decreased. With the present apparatus, however, flow to the patient can be increased to as great as 110 liters per minute and still maintain a temperature of greater than 90° F. at the patient. With all prior nebulizers at such a flow rate temperatures as high as 85° F. are difficult, if not impossible, to obtain. In prior nebulizers, as flow rate increases above 50 liters per minute, temperature decreases at a relatively fast rate. With the arrangement described herein, on the other hand, if flow rate is increased (by increasing the flow rate of oxygen provided to the mixer head), an increased amount of water is driven to the heated platen at the bottom of accumulator chamber 364 because of the increased pressure difference between chambers 362 and 364. Therefore, more water on the platen is vaporized and a greater amount of heat is added to the aerosol. Accordingly, with the described arrangement, as flow rate increases temperature may decrease, but will decrease at a significantly lower rate than it does with prior devices.

With the apparatus described in FIGS. 10 and 11, it is possible to provide an aerosol having 40 milligrams of water per liter of aerosol at the patient at a temperature of 94° F. In prior nebulizers, a maximum of 30 milligrams of water per liter was available at significantly lower temperatures.

A significant factor in the nebulizers described herein, particularly the embodiments of FIGS. 6 through 9 and FIGS. 10 and 11, is the fact that the instruments are configured and arranged for collecting particulate dropout and vaporizing the collected particulate so as to introduce heated water vapor into the aerosol, instead of sending the particulate dropout back into the container, as is the case with prior devices. In most prior devices little or no precipitated water droplets are heated, and almost none are vaporized for mixing with the aerosol. In the described arrangement, collection of particulate fallout is maximized, and all of the fallout may be fed to the heated bottom of the accumulator chamber for vaporization and re-introduction into the aerosol.

Operation of the nebulizers described herein, and in particular the nebulizer illustrated in Figs. 10 and 11, is carried out at total output flow rates (from output tube 210) in the range of about 15 to 80 liters per minute of moisturized gas. This output flow rate is controlled by the rate of flow of oxygen into the mixing body from the oxygen input tube, such as tube 134 of FIG. 6. With the input of oxygen controlled to provide a total output in the range of between about 15 and 80 liters per minute, the nebulizers described above operate in a fully satisfactory manner as described herein. However, in some applications the nebulizers may be operated to provide a total output flow outside of this range. Thus, for example, the input oxygen flow rate may be turned down sufficiently to cause a total output flow rate of less than 15 liters per minute. These nebulizers are sometimes used to provide total output flow rates as low as 8 liters per minute. In such a situation, at least in part because of the very low input oxygen flow, there is substantially no pressure differential across the gap between the lower end of the precipitate flow tube 170 or precipitate chamber inner wall 352 and the accumulator flow passage 172 (FIG. 6) and 364 (FIG. 10). Without this differential pressure droplets collected at the bottom of the precipitate chamber 362, for example, do not flow into the flow passage 364, and therefore the increase in water vapor which is achieved at higher total output flow rates by vaporization within the chamber 364, does not occur. At such lower total output flow rates there may be no water flowing along the heater platen 374 from the precipitate chamber, and therefore the output mixture may not be sufficiently moisturized by added water vapor in the accumulator chamber.

A somewhat analogous situation (e.g. lack of water vapor added in the accumulator chamber) occurs at very high total output flow rates, those above about 80 liters per minute. If the oxygen input rate is very high, or if a secondary gas (such as air) input is provided to the mixer body, as by an auxiliary pressurized air input of the nebulizer shown in U.S. Pat. No. 4,767,576 for Nebulizer With Auxiliary Gas Input, the pressure within the precipitate chamber 362 may be so high that an excess amount of water is driven by this pressure through the gap at the lower end of the inner wall 352. Under such conditions the flow passage 364 (FIG. 10) becomes filled or nearly filled with a body of turbulent water in a quantity too great for the heater to vaporize.

In operation within the normal total output flow range, between about 15 and 80 liters per minute, the pressure differential is such that water flows from the precipitate chamber 362 through the gap and into the flow passage 364 at a rate approximately equal to the rate at which the heater vaporizes water at the bottom of the accumulator chamber. In such a situation the differential pressure provides a relatively thin film or relatively small depth of water on the heater platen 374 within flow passage 364. Therefore only a small volume of water is presented to the heater platen at any given time for vaporization. For the vaporization of water by the heater to be most efficient and effective, the water flowing into the flow passage, which is effectively the vaporization chamber of the heater, must be at a rate sufficient to replace that which is vaporized by the heater. Moreover, water must not accumulate in such a volume within the flow passage 364 as to exceed the ability of the heater platen to vaporize the water. In other words, there may be inadequate vaporization by the heater when (a) there is no water on the heater platen with the accumulator chamber, or (b) there is too much water for the heater capacity.

Although adjustability of the gap between the lower end of inner circular wall 352 and the heated platen is available by means of the threaded interengagement of the heater housing and accumulator housing, such a fine adjustment by the user is not always possible in the field because the technician may have insufficient time or insufficient experience and training to establish the appropriate adjustment. Therefore it is desirable to provide for automatically controlled proper flow rate from the precipitate chamber to the accumulator chamber at all total output flow rates, including those below and above the range of 15 to 80 liters per minute.

Figure 12:
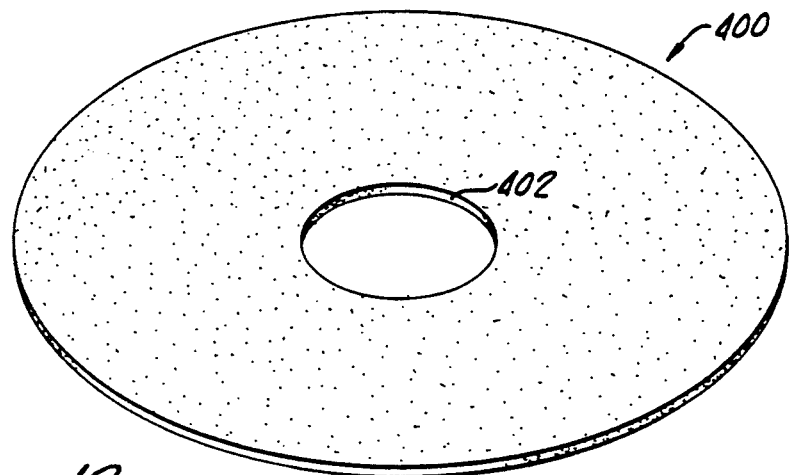
FIG. 12 is a pictorial illustration of a flow inducing control disc that may be used with any of the nebulizers described herein.
Figure 13:
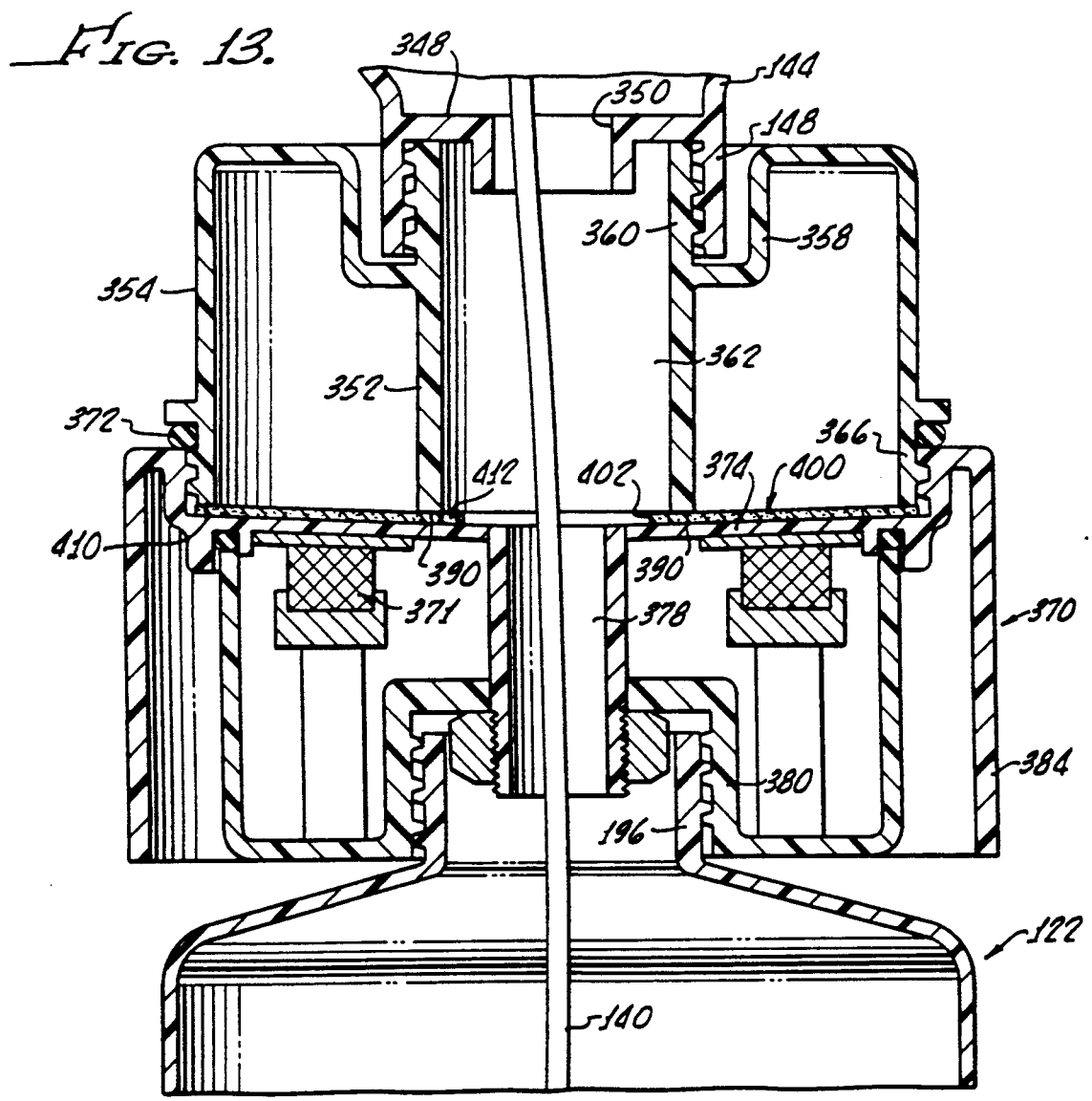
FIG. 13 is a vertical section of a portion of the embodiment of FIGS. 10 and 11 showing the flow inducing control disc of FIG. 12 on the heater platen.

Illustrated in FIGS. 12 and 13 is a slightly modified embodiment of the nebulizer of FIG. 10 in which the problems caused by total output flow rate that is either too low or too high are substantially avoided or at least significantly alleviated. This improvement is accomplished by inducing flow from the precipitate chamber 362 to the flow passage 364 and controlling the rate of such flow, to as to maintain at all times a suitable low depth of water on the heater platen within the accumulator chamber. To this end a flow inducing flow rate control member is positioned in the gap between the heater platen and the lower end of the circular inner wall 352 or the lower end of wall 170 of FIG. 8.

Conveniently, the flow inducing and flow rate control member is made of a mass transfer medium in the form of a capillary matrix. The capillary matrix is formed as a thin centrally apertured disc of a wicking material such as blotting paper, open cell foam or a porous solid. In a particular example a conventional chromatographic paper has been used. Preferably the wicking disc (of chromatographic paper) has a thickness of between about 5 and 30 mils in dry state (it may expand when wet). Water that is placed in contact with one portion of the disc is induced to flow to other portions of the material by wicking or capillary action. Such an annular disc is illustrated as a wicking disc 400 in FIG. 12, having an inner aperture 402 that is smaller in diameter than the diameter of inner circular wall 352 of the precipitate chamber of FIG. 10 and having an outer diameter that is substantially equal to the diameter of the outer wall 354 of the accumulator housing. The wicking disc 400 is merely inserted between the accumulator housing and the heater platen in the manner illustrated in FIG. 13. It just rests upon the platen. No parts of the heater or other parts of the assembly shown in FIG. 10 need be changed for use of the wicking disc 40. FIG. 13 shows parts of the nebulizer heater which are identical to and arranged in a manner identical to the corresponding parts of the embodiment of FIG. 10 The only difference between the devices of FIGS. 13 and 10 is the insertion in the device of FIG. 13 of the wicking disc 400. The disc is placed on the upper concave side of platen 374 and effectively held in place and clamped between the platen and the lower edges of the circular inner wall 352 and also clamped at the outer edges of the disc between the lower edges of the circular outer wall 354 and the outer edge of the platen 374.

The arrangement of the disc clamped between the accumulator housing and precipitate chamber on its upper side and the heater platen 374 on its lower side is illustrated in enlarged detail in FIG. 13. Thus, as can be seen in FIG. 13, lower edge 390 of the inner circular wall 352 clamps against an upper side of the wicking disc 400 radially outwardly of its inner edge 402. Similarly, a lower edge 410 of the outer circular wall 354 of the accumulator housing is pressed down against the upper side of the outer periphery of wicking disc 400, clamping this outer edge between the outer edge of the platen and the accumulator housing. An inner portion 112 of the disc lies in the precipitate chamber to receive precipitated droplets. Effectively, the wicking disc acts as a kind of a porous flow inducing barrier which prevents high flow rates of water through the gap (analogous to gap 202 of FIG. 8) between the wall end 408 and the heater platen.

With the arrangement of the wicking disc 400, as shown in FIGS. 12 and 13, a flow of water from the precipitate chamber 362 to the flow passage 364 along the platen and through the gap at the lower end of wall 352 is automatically maintained at an even controlled rate throughout a much wider range of total output flow rates. The flow induced by wicking action automatically adjusts its rate to replenish the water given up in the accumulator chamber to the aerosol by vaporization. The wicking disc operates to remain wet at all times, thus maintaining a volume of water on the heated platen that is within the power of the heater to vaporize. If the total rate of the nebulizer is less than 15 liters per minute, down to as low as 8 liters per minute or less, for example, so that there is little or no differential pressure to drive the water over the heater platen through the gap, the wicking action of the disc 400 is sufficient to induce flow of water from the precipitate chamber 362, through and along the wicking disc into the lower end of flow passage 364. The water that is caused to flow by the wicking action of the disc 400 effectively saturates the disc but does not flow at a rate sufficient to cause any significant amount of standing water on the upper surface of the disc within the flow passage 364. Effectively, the disc operates to remain saturated with water as long as there is water being provided to the inner portion of the disc, namely that portion indicated at 412 in FIG. 14, that is inward of the wall 352. As the heater heats the water contained in the outer portions of the wicking disc 400, within the flow passage 364, such water is vaporized and taken up by the aerosol mixture flowing through passage 364. As this water is vaporized the wicking action induces flow of additional water from the precipitate chamber, and thus a continuous flow of water from the precipitate chamber is induced by the wicking disc to automatically replenish water that is vaporized by the heat supplied by the heater. The wicking disc is effectively self-adjusting with regard to flow rate of water from the precipitate chamber to the flow passage and will operate at total aerosol output flow rates considerably below the normal 15 to 80 liters per minute flow rate.

Should the nebulizer be operated at very high total output flow rates, in the order of more than 80 liters per minute, so that a greater differential pressure is created, with a higher pressure within the precipitate chamber 362, the wicking disc acts as a flow controlling barrier that allows a limited amount of water to flow from the inner precipitate chamber to the outer flow passage. Thus, the presence of the wicking disc not only ensures some flow at very low total output flow rates, but prevents too great a flow at very high total output flow rates. Accordingly, over a greatly increased range of total output flow rates, the heater platen is provided with an optimum amount of water for most efficient vaporizing action.

As previously mentioned, the controlled flow rate induced by the wicking disc 400 cooperates with the heater and heated platen to maintain a relatively small volume of water covering the platen so that the heated platen vaporizes the water at approximately the same rate as the water is induced to flow through the wicking disc from the central precipitate chamber. The wicking member enhances the efficiency of the vaporization in several ways. First, it controls the depth of water above the platen and the rate of replenishment of water that is vaporized. In addition the wicking member provides a much greater surface area of water and of the capillary matrix itself to which heat from the platen may be transferred. Thus, a greatly increased surface area is provided to receive heat from the platen, and, effectively, a greater amount of water is thereby vaporized.

There have been described improved nebulizer heater assemblies which employ but a single heating unit to heat both the liquid in the nebulizer container and the aerosol produced by the nebulizer, while at the same time collecting rain out from the produced aerosol and reintroducing the collected rain out as water vapor into the aerosol.

The foregoing detailed description is to be clearly understood as given by way of illustration and example only, the spirit and scope of this invention being limited solely by the appended claims.

What is claimed is:

1. For use with a nebulizer having a mixing head including a mixing chamber for producing aerosol, said chamber having a lower connecting section with a lower opening therein, said chamber also having an outlet port for discharging aerosol, an improved heater assembly comprising:

- a heater chamber,
- a heater in said chamber,
- a heated platen extending across said heater chamber at an upper end thereof,
- an accumulator housing having:
  - an axially extending central chamber with a lower end adjacent said heated platen, said central chamber being configured and arranged to collect droplets of liquid precipitated from said aerosol,
  - an outer annular chamber circumscribing said central chamber, said annular chamber having input and output ports,
  - means on an upper portion of said accumulator housing for connecting said housing to said mixing head with said central chamber in communication with said lower opening of said lower connecting section of said mixing chamber, and means for flowing liquid collected in said central chamber to said outer annular chamber to be heated and vaporized by said heated platen, means on a lower portion of said accumulator housing for connecting said housing to said heater chamber with said platen forming a bottom of said outer annular chamber, and means for flowing aerosol from said outlet port into said annular chamber input port.

2. The heater assembly of claim 1 wherein said heated platen forms a bottom of said annular chamber, and wherein said central chamber lower end cooperates with said platen to define a gap, said gap forming said means for flowing liquid collected in said central chamber to said outer annular chamber.

3. The assembly of claim 2 including means for adjusting said gap to adjust rate of flow of liquid from said central chamber to said annular chamber.

4. The assembly of claim 1 wherein said heated platen is concave upwardly, and includes a drain port in a lowermost portion thereof.

5. The assembly of claim 1 wherein said central chamber is configured and arranged to be pressurized via said lower opening by a nebulizer mixing head connected to said accumulator housing, said heated platen having a low portion at said central chamber lower end, and having a drain in said low portion, whereby liquid droplets that fall out of said aerosol will flow through said lower opening of said mixing chamber into said central chamber, and whereby droplets collected in said central chamber will flow from the lower end of the central chamber into the annular chamber when the central chamber is pressurized, and will flow out through said drain port when said central chamber is not pressurized.

6. The heater assembly of claim 1 wherein said means for flowing liquid collected in said central chamber comprises means for inducing a controlled flow rate of liquid from said central chamber to said outer chamber.

7. The heater assembly of claim 6 wherein said means for inducing a controlled flow rate comprises a capillary matrix.

8. The heater assembly of claim 6 wherein said means for inducing a controlled flow rate comprises an annular disc of chromatography paper.

9. The heater assembly of claim 6 wherein said means for inducing a controlled flow rate comprises an annular disc of blotter paper.

10. The heater assembly of claim 6 wherein said means for inducing a controlled flow rate comprises an annular disc of a capillary matrix.

11. The heater assembly of claim 6 wherein said means for inducing a controlled flow rate comprises a wicking disc interposed between the lower end of said central chamber and said platen.

12. The heater assembly of claim 1 wherein said central chamber lower end cooperates with said platen to define a gap, and including a body of a mass transfer material positioned in said gap and extending on both sides of said gap.

13. A heater assembly comprising:

a heater chamber, a heater in said chamber, a heated platen extending across said heater chamber at an upper end thereof, an accumulator housing having a wall dividing the housing into a precipitate chamber and a flow passage, said precipitate chamber including means for receiving liquid, said accumulator flow passage including means for receiving a gas mixture and means for discharging said mixture therefrom, and means for inducing flow of liquid from said precipitate chamber to said flow passage.

14. The heater assembly of claim 13 wherein said means for inducing flow comprises a capillary matrix.

15. The heater assembly of claim 13 wherein said means for inducing flow comprises a body of wicking material extending from said precipitate chamber to said flow passage.

16. The heater assembly of claim 13 wherein said means for inducing flow includes means for limiting flow from said precipitate chamber to said flow passage.

17. The heater assembly of claim 13 wherein said means for inducing flow includes means for covering said platen with a relatively small volume of liquid, whereby said heated platen may vaporize liquid covering the platen at a rate substantially equal to the rate of flow of liquid from said precipitate chamber to said flow passage.

18. The heater assembly of claim 13 wherein said mean for inducing flow comprises means cooperating with said heater to maintain a relatively small volume of liquid covering said heater platen.

19. For use with a nebulizer having a mixing head including a mixing chamber for producing aerosol, said chamber having a lower connecting section with a lower opening therein, said chamber also having an outlet port for discharging aerosol, an improved heater assembly comprising:

a heater chamber, a heater in said chamber, a heated platen extending across said heater chamber at an upper end thereof, an accumulator housing having:

a central precipitate chamber configured and arranged to collect droplets of liquid precipitated from said aerosol, an outer chamber circumscribing the central chamber and having input and output ports, means on an upper portion of the accumulator housing for connecting the housing to a mixing head, with said central chamber in communication with the lower opening of the lower connecting section of the mixing chamber, and means for inducing flow of liquid at a controlled flow rate from said central chamber to said outer chamber to be heated and vaporized by said heated platen, and means on a lower portion of said accumulator housing for connecting said housing to said heater chamber with said platen forming a bottom of said outer chamber.

20. The heater assembly of claim 19 wherein said means for inducing flow comprises a flow passage between said central chamber and outer annular chamber and mass transfer means in said flow passage.

21. The heater assembly of claim 20 wherein said mass transfer means includes a body of wicking material extending from a point within said central chamber to a point in said outer annular chamber.

22. The heater assembly of claim 21 wherein said body of wicking material lies along an upper surface of said heated platen.

23. The heater assembly of claim 19 wherein said heated platen has an upper surface forming a bottom of said outer chamber, and wherein said means for inducing flow comprises an annular wicking disc extending from said central chamber to said annular chamber and having a portion thereof lying on said upper surface of said heated platen within said annular chamber.

24. The heater assembly of claim 19 wherein said heated platen has an upper surface forming a bottom of said annular chamber, wherein said central precipitate chamber has a lower end positioned adjacent to but spaced from said heated platen surface, and wherein said means for inducing flow comprises a flow inducing member extending along said heated platen surface between said lower end of aid central precipitate chamber and said heated platen surface.

25. The heater assembly of claim 19 wherein said heated platen has an upper surface forming a bottom of said outer annular chamber and wherein said central precipitate chamber has a lower end positioned adjacent to and spaced from said heated platen upper surface, said means for inducing flow comprising a thin disc of a capillary matrix positioned in contact with said heated platen surface and extending between said surface and said lower end of said central chamber from a position within said central chamber to outer portions of said heated platen.

26. A heater assembly comprising:

an accumulator housing defining an accumulator chamber having input and output ports, said accumulator chamber including means for receiving an aerosol mixture of gas and liquid vapor at said input port and discharging said mixture from said output port.

a precipitate collection chamber having a precipitate input port adapted to receive liquid precipitate, heating means for vaporizing liquid in said accumulator chamber, and means for inducing liquid flow at a controlled rate from said precipitate collection chamber to said accumulator chamber.

27. The heater assembly of claim 26 wherein said means for inducing liquid flow comprises a wicking member extending between said precipitate collection chamber and said accumulator chamber.

28. The heater assembly of claim 26 wherein said heating means includes a heater platen, and wherein said means for inducing liquid flow comprises a capillary matrix extending from said precipitate collection chamber to said accumulator chamber and having a portion in contact with said heater platen.

* * * * *